United States Patent [19]
Francis

[11] Patent Number: 5,897,543
[45] Date of Patent: *Apr. 27, 1999

[54] FILM

[75] Inventor: Michael A. Francis, Midlothian, Va.

[73] Assignee: Tredegar Industries, Inc., Richmond, Va.

[*] Notice: This patent is subject to a terminal disclaimer.

[21] Appl. No.: 08/727,326

[22] Filed: Oct. 8, 1996

Related U.S. Application Data

[63] Continuation of application No. 08/259,397, Jun. 14, 1994, abandoned.

[51] Int. Cl.$^6$ .............................. A61F 13/15; B32B 3/24
[52] U.S. Cl. ..................... 604/383; 604/378; 604/370; 428/131; 428/132; 428/137; 428/156
[58] Field of Search .................... 604/358, 370, 604/378, 383, 385.1; 428/131, 132, 137, 156

[56] References Cited

U.S. PATENT DOCUMENTS

| | | | |
|---|---|---|---|
| 3,054,148 | 9/1962 | Zimmerli . | |
| 3,709,647 | 1/1973 | Barnhart . | |
| 3,814,101 | 6/1974 | Kozak . | |
| 3,929,135 | 12/1975 | Thompson | 604/383 |
| 4,151,240 | 4/1979 | Lucas et al. . | |
| 4,155,693 | 5/1979 | Raley . | |
| 4,252,516 | 2/1981 | Raley et al. . | |
| 4,319,868 | 3/1982 | Riemersma et al. . | |
| 4,324,246 | 4/1982 | Mullane et al. | 604/370 |
| 4,341,217 | 7/1982 | Ferguson et al. | 604/370 |
| 4,351,784 | 9/1982 | Thomas et al. . | |
| 4,388,056 | 6/1983 | Lee et al. . | |
| 4,535,020 | 8/1985 | Thomas et al. | 604/383 |
| 4,543,299 | 9/1985 | Raley et al. . | |
| 4,585,156 | 4/1986 | Raley et al. . | |
| 4,636,161 | 1/1987 | Raley et al. . | |
| 4,644,623 | 2/1987 | Raley et al. . | |
| 4,846,813 | 7/1989 | Raley | 604/378 |
| 5,383,870 | 1/1995 | Takai et al. | 604/378 |
| 5,591,510 | 1/1997 | Junker et al. | 604/378 |

FOREIGN PATENT DOCUMENTS

| | | | |
|---|---|---|---|
| 0172420 | 2/1986 | European Pat. Off. | 604/358 |
| 9309741 | 5/1993 | WIPO | 604/378 |

*Primary Examiner*—John G. Weiss
*Assistant Examiner*—Dennis Ruhl
*Attorney, Agent, or Firm*—Jenkens & Gilchrist, P.C.

[57] ABSTRACT

The invention is directed to a thermoplastic film having a first surface and a second surface. The second surface is spaced apart from the first surface. A plurality of perforations extend through the film from the first surface to the second surface. The perforations form capillaries that extend from the second surface. The capillaries are disposed at an angle from about 5° to about 60° with respect to a plane that is perpendicular to the first surface.

12 Claims, 7 Drawing Sheets

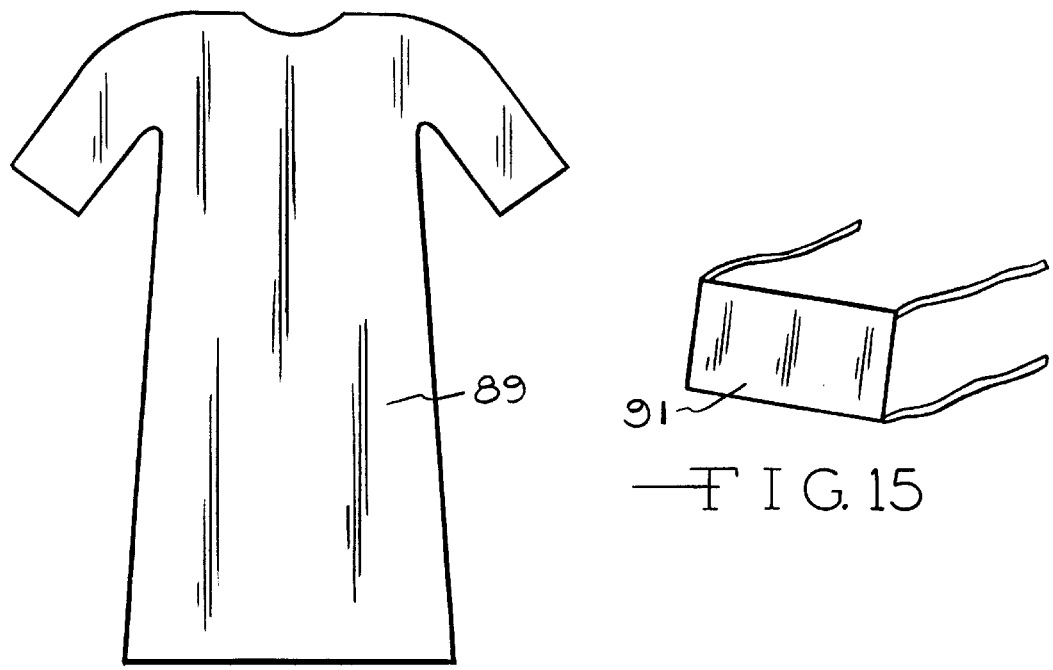
FIG. 14
FIG. 15
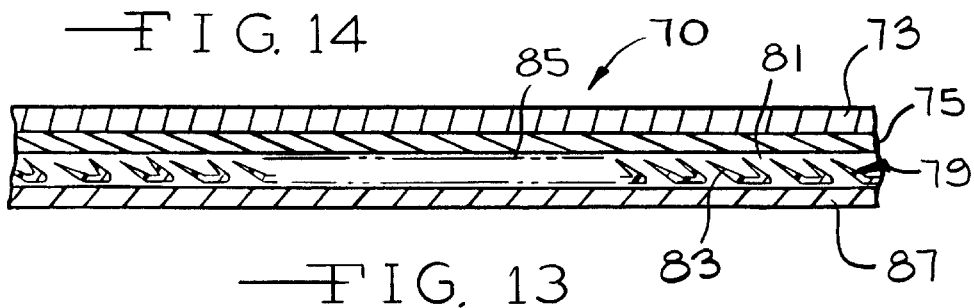
FIG. 13
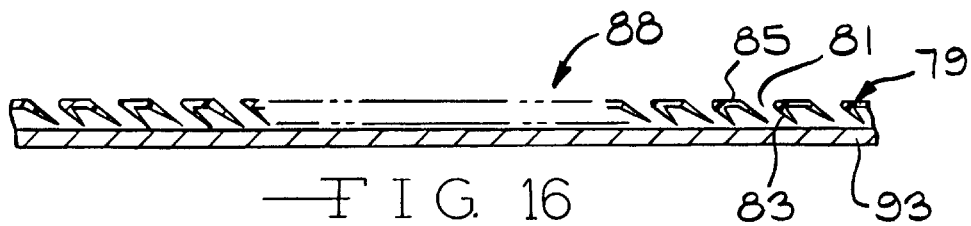
FIG. 16
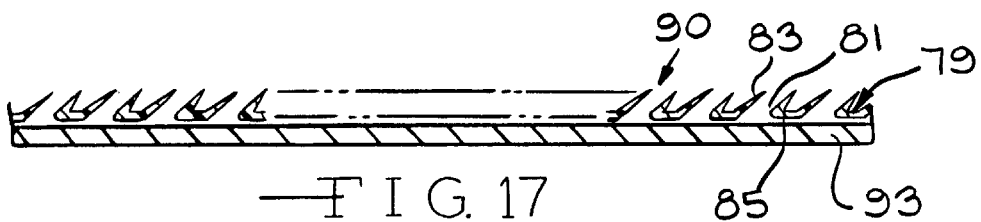
FIG. 17
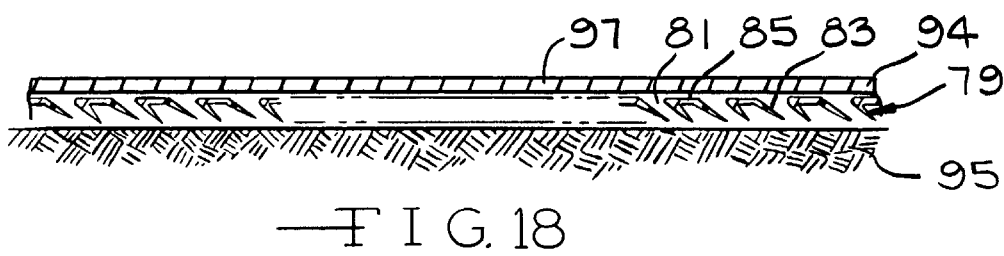
FIG. 18

FILM

This application is a continuation of application Ser. No. 08/259,397 filed on Jun. 14, 1994 now abandoned.

BACKGROUND ART

The present invention is in the general field of perforated plastic film and especially relates to perforating of plastic film. The invention particularly relates to perforated plastic film, the metal screens or molding elements used in the vacuum perforation of plastic film and to a method of fabricating such screens.

Perforated plastic film has many useful applications. It is used in gardening and farming to prevent the growth of grass and weeds while permitting moisture to be transmitted through the film to the soil beneath. Perforated films have a multiplicity of regularly spaced apertures which allow permeation of liquid and air or other fluids. Such films can be used as a component of disposable garments for sanitary apparel purposes, such as napkins, diapers, or for hospital pads, bed or sleeping bag linings, and the like. In such composite structures, an exterior layer of film having the desired properties is provided which would be adjacent to the skin in a composite garment, and the garment would also include a filler layer or layers of absorbent fibrous material. An example of the use of perforated film for making disposable diapers is shown in U.S. Pat. No. 3,814,101.

A particular class of perforated film is described by Thompson, U.S. Pat. No. 3,929,135, issued Dec. 30, 1975. Thompson teaches an absorptive structure with a top layer of perforated film characterized by having a series of regular spaced small apertures in the form of tapered capillaries of certain dimensions ranges. In the finished article, these are directed inwardly to be in intimate contact with an absorbent fibrous material layer. The smooth side of the perforated film is thus in use in contact with the skin. Film as described by Thompson, in garment structure as outlined, maintains a dry and comfortable condition, even after transmission of fluids to the absorbent layer by the combined effects of the absorption and the resistance to back flow as a result of the relative length and surface properties of the tapered capillaries.

One of the earlier methods for vacuum perforation of plastic film is disclosed in U.S. Pat. No. 3,054,148. The patentee describes a stationary drum having a molding element or screen mounted around the outer surface of the drum and adapted to freely rotate thereon. A vacuum chamber is employed beneath the screen to create a pressure differential between the respective surfaces of the thermoplastic sheet to be perforated to cause the plasticized sheet to flow into openings provided in the screen and thereby cause a series of openings, holes or perforations to be formed in the plastic sheet or film.

One method for making film with tapered capillaries on one side thereof is shown in U.S. Pat. No. 3,054,148 issued Sep. 18, 1962, to Zimmerli. In this patent heated film is supported by a perforated screen and a vacuum applied to the underside of the perforated screen. Holes are pulled in the film in the direction of the vacuum beneath the screen thereby forming tapered capillaries in the film.

A variety of methods and apparatuses including particular types of perforating screens or rotatable molding elements have been developed over the years for particular perforation operations. Examples of these are U.S. Pat. Nos. 4,155,693; 4,252,516; 3,709,647; 4,151,240; 4,319,868 and 4,388,056. In U.S. Pat. No. 4,155,693, the screen is comprised of a series of perforated metal strips preferably welded together to form a cylinder. U.S. Pat. No. 4,252,516 provides a screen having a series of hexagonal depressions with elliptical holes centered therein. U.S. Pat. No. 3,709,647 provides for a rotating vacuum-forming roll having a circulating cooling medium therein.

U.S. Pat. No. 4,151,240 provides a means for cooling the film after it has been perforated and debossed. U.S. Pat. No. 4,319,868 sets forth an apparatus for making a thermoplastic film having raised bosses with perforated tips. A particularly constructed embossing roll for effecting the desired film pattern is disclosed. U.S. Pat. No. 4,388,056 discloses an apparatus for continuously forming an air-laid fibrous web having oppositely phased, cylindrically undulating side edges and a predetermined basis weight distribution. An air-laying drum has a honeycomb-type annular-shape frame including circumferentially extending ribs and transverse plates. A stationary adjustable air flow modulating means is disposed adjacent the radially inwardly disposed boundary of an arcuate portion of a circumferentially segmented annularshape plenum, circumferentially spanning a plurality of plenum segments for adjusting a pressure drop across particular areas of the surface of the air-laying drum.

Vacuum perforation of thin plastic films involves the extrusion of molten polymeric materials such as polyethylene and other plastic polymers through a die. The hot melt web of film or plastic sheet exiting the die impinges on a rotating cylindrical screen which is mounted on a stationary vacuum drum or roll. The vacuum roll has an axial slot and a set of seals extending longitudinally along the length of its inside surface, beneath the area where the web of plastic impinges on the screen or molding element. A vacuum from inside the screen is directed through the slot in the vacuum roll. The vacuum present within the slot forms or molds the plastic film or sheet to the screen and perforates it through the holes of the screen. At the same time, an airflow is produced which cools the film.

An important component of the vacuum processing equipment is the cylindrical screen. This molding element defines aesthetic, tactile and mechanical properties of the film as well as the geometric pattern of the perforated film. In a preferred screen fabrication technique, the desired screen pattern is nickel plated on a specially prepared cylindrical mandrel. A seamless cylindrical nickel screen of any predetermined or desired pattern can be produced. Other metals, such as copper may also be used.

However, the prior art screens produce film with perforations that extend through the film at substantially a right angle to the surface of the film. Such perforations provide a direct line of sight and a direct path through the film. This feature of the prior art film is undesirable when the film is used in catamenial or incontinent applications as the collected fluid remain visible. Accordingly, there is a need for a perforated film having masking characteristics that reduce the visible presence of the collected fluids.

It is also desirable to have a film that does not provide a direct path through the film for fluids. Such a film can be utilized for protective clothing as fluids contacting the surface of the film will not have a direct path through the film. Such a characteristic greatly improves the protective quality of the clothing.

DISCLOSURE OF THE INVENTION

The invention is directed to a thermoplastic film having a first surface and a second surface. The second surface is spaced apart from the first surface. A plurality of perforations extend through the film from the first surface to the second surface. The perforations form capillaries that extend from the second surface. The capillaries are disposed at an angle from about 5° to about 60° with respect to a plane that is perpendicular to the first surface.

BRIEF DESCRIPTION OF THE DRAWINGS

FIG. 13 is a cross-sectional view of a fabric containing the perforated film of the present invention.

FIG. 14 is a protective gown using the fabric of FIG. 13.

FIG. 15 is a facemask using the fabric of FIG. 13.

FIG. 16 is a cross-sectional view of an absorbent pad or drape.

FIG. 17 is a cross-sectional view of an absorbent pad or drape.

FIG. 18 is a cross-sectional view of a landscape fabric.

BEST MODE OF CARRYING OUT THE INVENTION

Figure 1:
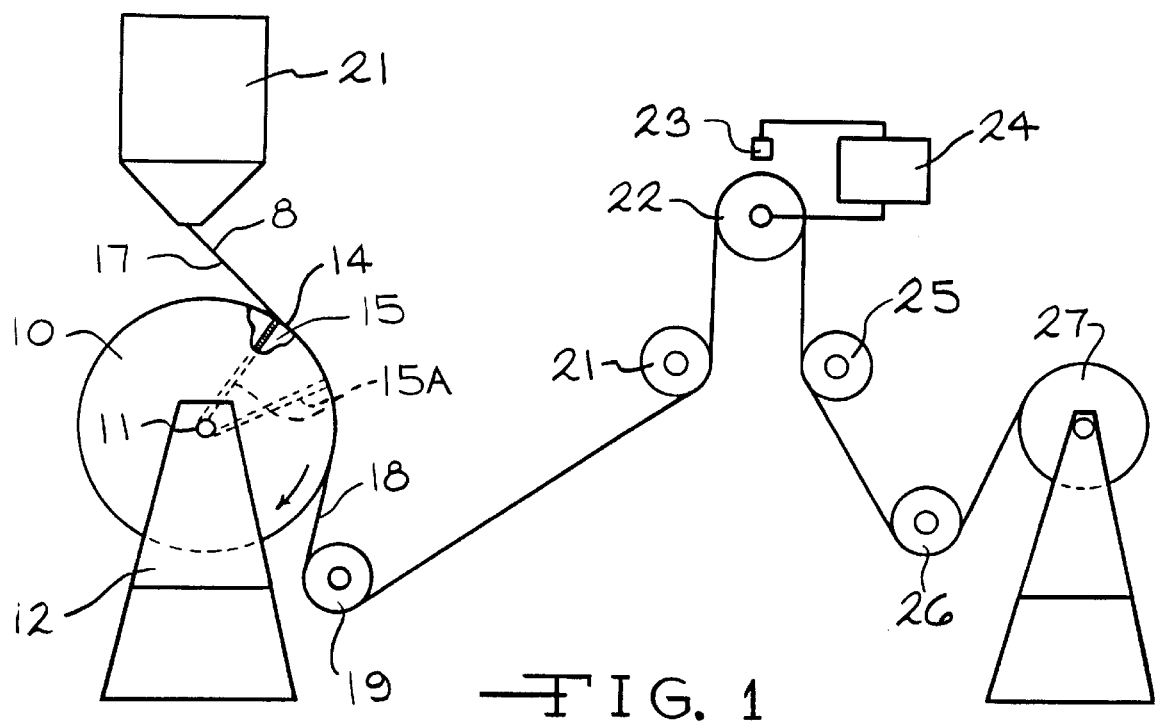
FIG. 1 is a schematic elevational view showing the interrelationship of the principle pieces of equipment employed in carrying out the process.

Referring to FIG. 1, an apparatus for carrying out the process of the invention includes a rotary cylindrical drum 10 supported at each end by a centrally disposed axle 11 supported by means of stationary axle supports 12. The cylindrical surface 13 of drum roll 10 is highly perforated to allow air to pass therethrough. The molding element or screen 14 is mounted around the surface 13 of drum 10 and is adapted to rotate with the drum 10.

Element 14 may be formed as an integral unit adapted to be slipped on drum 10 from an end thereof or it may be wrapped around the drum 10 and then affixed thereto in any suitable manner. For purposes of rotating drum 10, a gear drive may be employed which is adapted to mesh with gearing provided on the drum element itself or a pulley drive may be connected to the drum by means of caps provided on the ends thereof. As shown in FIG. 1, a vacuum chamber 15 is utilized to create a pressure differential between the respective surfaces of the thermoplastic sheet to cause the plasticized sheet to flow into the perforations provided in the molding element 14 and therefore perforate the sheet.

Figure 2:
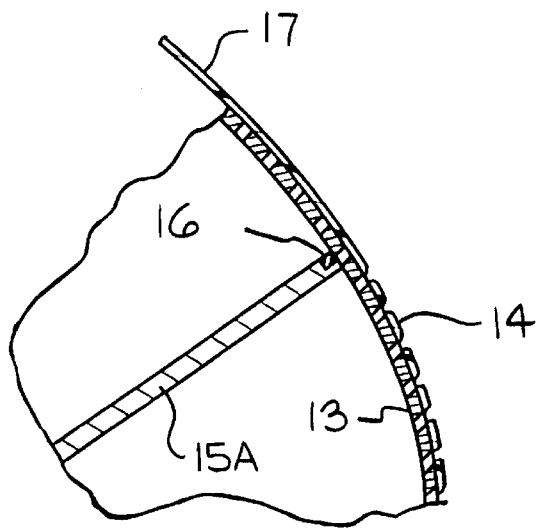
FIG. 2 is an enlarged, sectional view showing a segment of the forming surface as employed in the process.

Referring to FIGS. 1 and 2, the vacuum chamber 15 is positioned within drum 10, along the axis of drum 10 and opens at the surface of the drum over a limited portion of its periphery in contact with the inner portion of surface 13 of drum 10. Two plates 15A define the chamber. In order to provide an effective seal of the leading and trailing edges of chamber 15, seals 16 are provided in plates 15A to form a seal against the surface 13. The seals may be made of metal, HDPE, rubber or other suitable material. The plates 15A are stationary with respect to the rotational direction of the drum and rigidly affixed to axle 11 or other suitable means so that chamber 15 remains in a fixed or stationary position in drum 10. Thus, chamber 15 is sealed at all points except the peripheral openings on drum 10 and may be evacuated or reduced in pressure by pumping equipment connected to the chamber in any suitable manner.

As can be seen in FIG. 1, located above and adjacent to drum 10 is extruder 21 having a die 8 which is used to extrude a hot thermoplastic sheet 17 onto drum 10. In practice it has been found that polyolefin materials work particularly well as the thermoplastic material that is extruded onto the drum 10. As the sheet material 17 travels downwardly from die 8, the sheet contacts screen 14 which is turning clockwise with drum 10 in FIGS. 1 and 2. The rotating screen 14 carries sheet 17 over vacuum slot 15 which causes the thermoplastic material to be drawn into the openings in screen 14 and thereby perforated. The sheet is cooled to change the hot thermoplastic material from its molten state to a solid state and to set the perforations in the film. The sheet 17 continues to travel around in a clockwise manner shown in FIG. 1 on drum 10 and continues on to the rolls 19.

From roll 19 the solid sheet material 18 continues upwardly over roll 21 to corona treating roll 22. The corona treating roll 22 is usually covered with a suitable dielectric material such as epoxy, fluorinated polyethylene (TEFLON), chlorinated polyethylene (HYPALON), OR POLYESTER (MYLAR). However, bare roll treating with a dielectric covered electrode can be utilized to treat the film. The electrode or corona bar 23 is suspended parallel to the treater roll at about 1/16 of an inch above the roll. The corona bar 23 is energized by a transformer and corona treating power source 24. The sheet continues past a tension roll 25 to a second tension roll 26 and onto wind-up roll 27. It should be understood that the corona treating operation is not required for all applications for the film and this part of the process can be removed. Further, it is not always necessary to wind the film onto a wind-up roll 27 if the film is being put into an end use application in an in-line process.

It should be noted that other forming processes can be utilized to form the perforated plastic films of the present invention. The process shown in U.S. Pat. No. 4,878,825 which utilizes a support for the forming screen in the area of the vacuum slot works particularly well in forming the perforated film of the present invention. The process shown in U.S. Pat. 4,839,216 that utilizes a high-pressure liquid stream to perforate a plastic film can be also used with the present invention. The teachings of U.S. Pat. Nos. 4,878,825 and 4,839,216 are hereby expressly incorporated by reference into this patent application as alternative methods for forming the perforations of the present invention.

Figure 3:
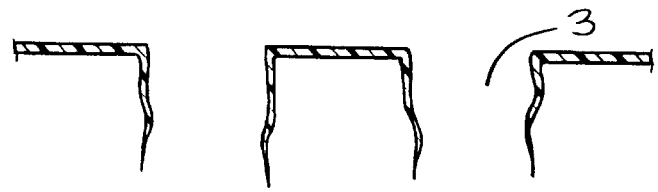
FIG. 3 is an enlarged, schematic, sectional view of a prior art perforated film having straight capillaries.
Figure 4:
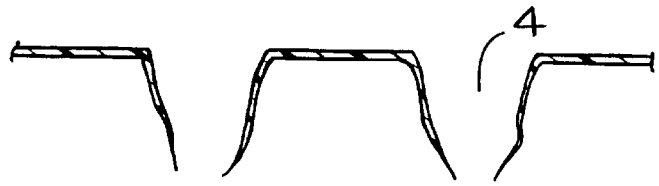
FIG. 4 is an enlarged, schematic, sectional view of a prior art perforated film having tapered capillaries.

FIGS. 3 and 4 show prior art types of perforated plastic films that have been produced on the apparatus shown in FIG. 1. This film has straight capillaries 3 as shown in FIG. 3, or tapered capillaries 4 as shown in FIG. 4. In both of these films, the perforations are disposed at substantially a 90° angle with respect to the surface of the film and provide a direct line of sight and a direct path through the film.

Figure 5:
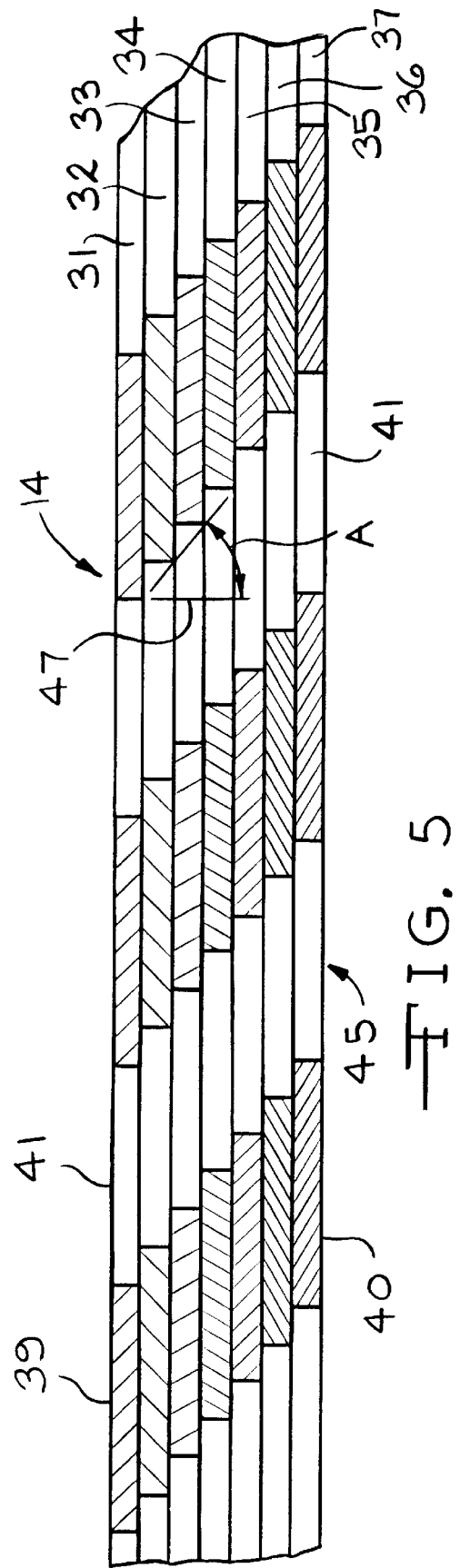
FIG. 5 is a cross-sectional view of a film forming screen of the present invention.

One configuration for the screen 14 of the present invention which is utilized to form the perforated plastic film is shown in more detail in FIG. 5. The screen 14 is a laminate structure comprised of a stack of individual sheets 31, 32, 33, 34, 35, 36, and 37. The screen 14 has an outer surface 39 that is disposed to be in contact with the thermoplastic sheet 17 and an inner surface 40 that faces the vacuum chamber 15. The sheets contain a plurality of apertures 41 that extend through the thickness of the individual sheets. The apertures 41 preferably all have substantially the same geometric shape, however, it should be understood that the shapes of the apertures can be different. The sheets are normally a stainless steel, photo-etched metallic material where the photo-etching has formed the apertures 41 in the individual sheets. The sheets generally have a thickness from about 1 to about 5 mils. In practice it has been found that sheets having a thickness of about 2 mils work particularly well. Usually from about 2 to about 20 sheets are used to form the screen 14. The preferred range for the number of sheets to form a screen 14 is from about 4 to about 10 sheets. The effective diameter of the apertures 41 in the sheets is from about 2 mils to about 100 mils. In practice it has been found that a range from about 7 mils to about 60 mils for the effective diameter of the apertures 41 works particularly well. The sheets of the laminate are bonded to one another at contact points while the laminate is subjected to heat and pressure. The resultant laminate structure is thereafter rolled into a tubular shape and its free edges are bonded to one another to form a continuous tubular-forming structure. As shown in FIG. 5, the apertures 41 in the laminate structure are not concentrically aligned. Instead, the apertures 41 are circumferentially displaced in the same direction to form a passageway 45 through the laminate structure that is disposed at an angle. The apertures 41 shown in FIG. 5 all have substantially the same diameter and each aperture has been displaced from about 1% to about 50% of the diameter of the apertures from the aperture on the adjacent sheet with a preferred range of 5% to 25% of the diameter of the apertures. In practice it has been found that a displacement of about 10% of the diameter of the apertures works particularly well. This results in a passageway 45 that is disposed at an angle from about 5° to about 60° with respect to a plane or line 47 which extends perpendicular to the outer surface 39 of the screen 14. This angle is generally shown as angle A in FIG. 5.

The apertures 41 in the sheets are generally circular in shape and the passageway 45 formed through the laminate screen 14 is generally cylindrical in shape. However, it should be understood that shapes for the apertures can vary and that oval, ellipsoidal and other shapes can be used, and multi-sided figures such as a rectangle, square, hexagon or a pentagon can be utilized for the openings.

Figure 10:
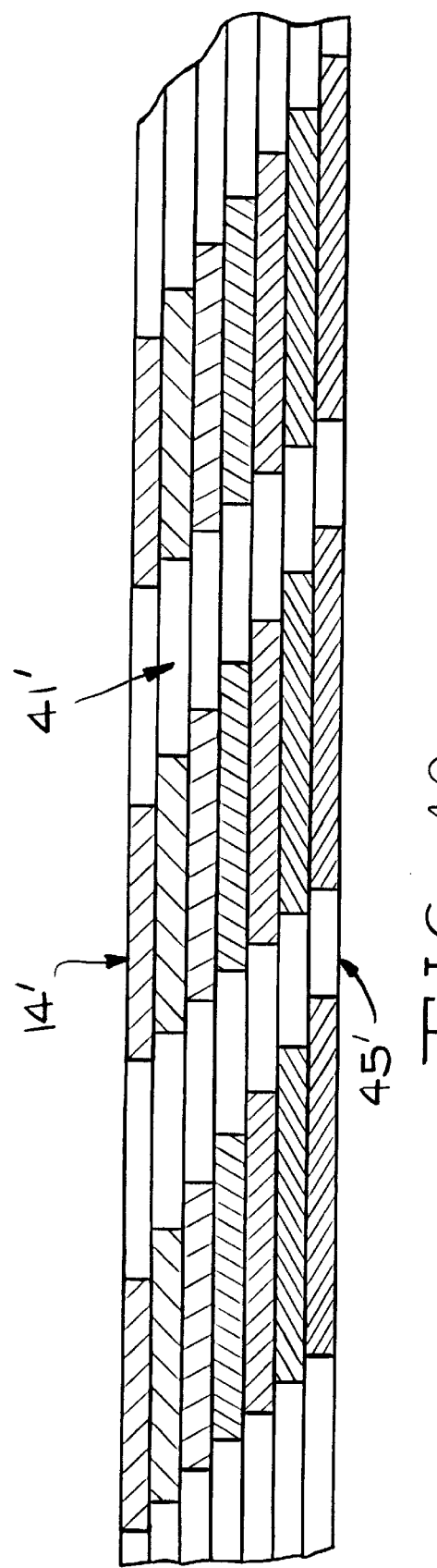
FIG. 10 is a cross-sectional view of a film forming screen.

As shown in FIG. 10, the screen 14' has apertures 41' that become progressively smaller in each adjacent sheet of the laminate. In this screen structure, the passageway 45' that is formed will converge as the passageway advances through the screen 14'. In this particular structure each aperture 41' is displaced a selected percentage of its diameter from the apertures on adjacent sheets. This results in a passageway 45' that continuously and uniformly converges as the passageway advances through the screen 14'.

Figure 11:
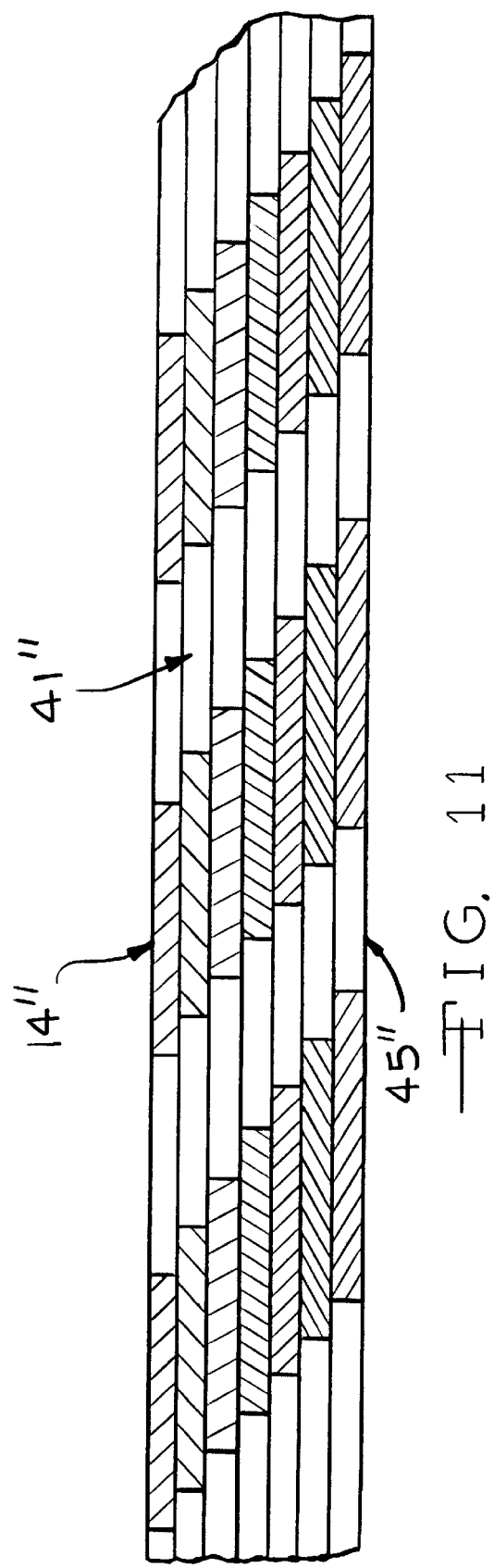
FIG. 11 is a cross-sectional view of a film forming screen.

The screen 14" shown in FIG. 11 has apertures 41" that become progressively smaller as the apertures shown in FIG. 10. However, in FIG. 11, the apertures 41" are displaced in the screen 14" as that the passageway 45" converges in one direction as the passageway advances through the screen 14".

Figure 12:
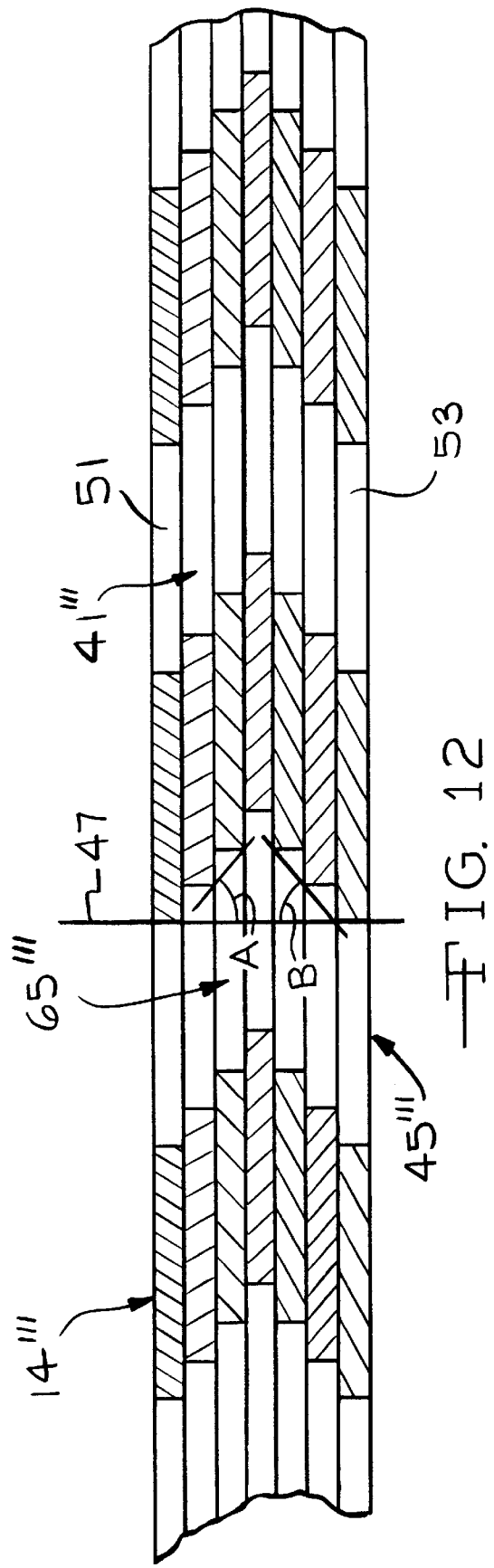
FIG. 12 is a cross-sectional view of a film forming screen.

As shown in FIG. 12, the screen 14''' defines a passageway 45''' that has a compound curve for the passageway. In this embodiment a portion of the sheets that form the screen 14''' are displaced in one direction to form a first portion 51 of the passageway 45''' and a plurality of sheets are displaced in the opposite direction to form a second portion 53 for the passageway 45'''. Normally, all of the apertures 41''' will be of the same diameter and will be displaced a equal distance on each layer of the screen 14'''. However, it should be noted that the apertures 41''' can vary in size and the amount of displacement can vary to form a converging passageway 45'''. The first portion 51 of the passageway 45'''is disposed at an angle A that is from about 5° to about 60° with respect to a line or plane 47' which extends perpendicular to the outer surface 39''' of the screen 14'''. The second portion 53 is disposed at an angle B that is from about 5° to about 60° with respect to the plane or line 47.

Figure 6:
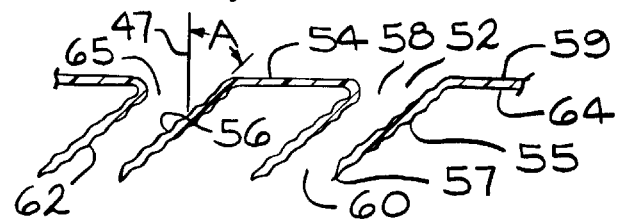
FIG. 6 is a cross-sectional view of a perforated film made using the screen of FIG. 5.

FIG. 6 shows a cross section of a film 54 that has been formed utilizing the screen shown in FIG. 5. The film 54 has a first surface 59 and a second surface 64. The first and second surfaces of the film are usually positioned in substantially parallel relationship. This film has a plurality of perforations 52 that form capillaries 55 in the film. The capillaries 55 have a substantially uniform diameter and are displaced at an angle A from about 5° to about 60° with respect to a plane 47 that is perpendicular to the first surface 59 of the film. The capillaries 55 are substantially cylindrical in shape, have a side wall 62, define a passageway 65, have first opening 58 in the surface 59 of the film 54 and second opening 60 at the end 57 of the capillary 55 that is spaced apart from the first surface 59 of the film 54. The ends 57 of the capillaries 55 are usually spaced apart from the surface 59 of the film 54 by a distance from about 0.005 to about 0.05 of an inch with a spacing from about 0.007 to about 0.025 of an inch being preferred. The opening 58 and the opening 60 both have a center point or geometric center and the center point of opening 58 is displaced from the center point of opening 60. The center point of opening 60 is displaced from the center point of opening 58 by a distance that is from about 5% to about 200% of the diameter of the opening 60 with the preferred range being from about 75% to about 125% of the diameter of the openings 60. As can be seen in FIG. 6, the capillaries 55 have a plurality of steps or ridges 56 that are produced by the off-set sheets of the screen 14. The ridges 56 in the film 54 are substantially rounded instead of the sharp corners formed by the off-set sheets that form the screen 14.

Figure 9:
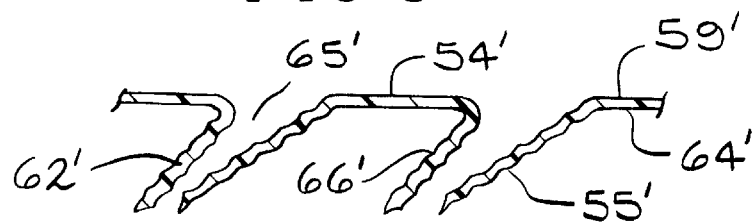
FIG. 9 is a cross-sectional view of a perforated film made using the screen of FIG. 10.

FIG. 9 shows the cross section of a film 54' that has been formed utilizing the screen shown in FIG. 10. This film 54' is substantially similar to the film shown in FIG. 6 except that the side wall 62', each capillary 55' and the passageway 65' converge as it extends from the first surface 59' of the film.

Figure 7:
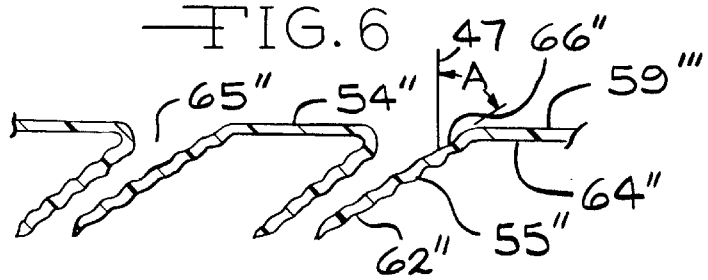
FIG. 7 is a cross-sectional view of a perforated film made using the screen of FIG. 11.

FIG. 7 shows a cross section of a film 54" that has been produced using the screen in FIG. 11. In this film the side wall 62" of the capillaries 55" and the passageway 65" converges as it advances away from the surface of the film and in particular converges on one side in one direction.

Figure 8:
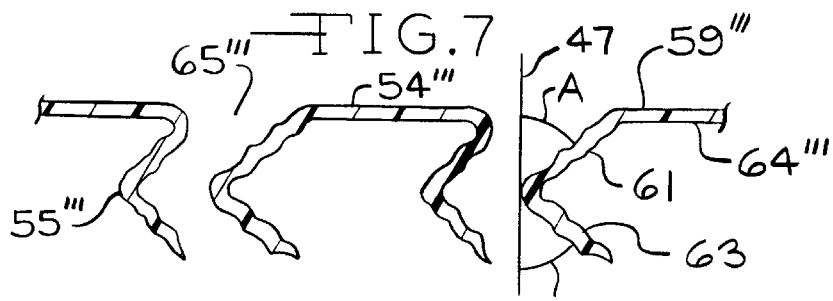
FIG. 8 is a cross-sectional view of a perforated film made using the screen of FIG. 12.

FIG. 8 shows a cross section of a section of film 54''' produced utilizing the screen shown in FIG. 12. In this figure the capillaries 55''' and the passageway 65''' have a first portion 61 that is disposed at an angle A with respect to a plane 47 that is disposed perpendicular to the first surface 59''' of the film and a second portion 63 that is disposed at an angle B and both angles are from about 5° to about 60° with respect to the plane 47. In FIG. 8 the capillary 55''' generally converges as it advances from the first surface 59''' of the film 54'''. However, it should be understood that the capillaries 55''' can have walls that do not converge.

The above films all have capillaries that are disposed at an angle that acts to block a direct line of sight through the apertures that is perpendicular to the surface of the film. Accordingly, the films will have a masking characteristic such that fluids that pass through the film to an absorbent structure will not be as visible to a user as when the capillaries are perpendicular to the first surface 59 of the film. This is particularly important for catamenial or incontinent applications. The degree of masking produced by the film will be directly proportional to the angle of the capillaries in the film, their length and the degree to which the capillaries converge in shape. Such films also can be useful in preventing unwanted direct fluid flow through the film. Since the capillaries are disposed at an angle, fluid striking the surface of the film will not have a direct path through the film. Instead, the fluid will have to change direction to pass through the capillaries. Such film can be used for protective clothing when fluids may come into direct contact with the surface of the protective clothing. The film of the present invention will reduce the tendency of the fluid from splashing directly through the capillaries and greatly enhance the protective capability of the clothing.

FIG. 13 shows a layered fabric material that utilizes the film of the present invention. The layered fabric material 70 has a light weight, breathable outer layer 73. The outer layer 73 is usually a paper cover stock that is very light weight and also highly breathable. Next is a layer of non-woven material 75 that is breathable, but provides resistance to the passage of fluids through this layer. In particular, the non-woven material provides good resistance to flow for liquids that come in contact with the non-woven material. A melt blown polypropylene, polyethylene or polyester can be used for the non-woven layer as these materials have acceptable levels of fluid resistance. The next layer on the fabric 70 is a thermoplastic film 79 that has a plurality of perforations 81 and the perforations form capillaries 83 and they are disposed at an angle from about 5° to about 60° with respect to a plane that is perpendicular to the surface 85 of the film. The thermoplastic film 79 is positioned so that the capillaries 83 extend toward and are in contact with the non-woven material. The capillaries 83 formed by the perforations 81 allow the film 79 to be breathable while resisting the direct flow of liquid through the film. Although the film 79 has been shown as being substantially similar to the film 54 shown in FIG. 6, it should be understood that the film similar to the films shown in FIGS. 7, 8 and 9 can also be used for the film 79 in the layer fabric material 70. The next layer in the layered fabric 70 is a second layer of non-woven material 87 that is positioned adjacent the surface 85 of the film 79. The second layer of non-woven material 87 is intended to be a layer that comes into contact with the skin of the user of the fabric material 70. If the fabric material is not intended to come into contact with the skin of the user, the second layer of non-woven material 87 can be deleted.

The purpose of the fabric material 70 is to provide a breathable structure that has good resistance to penetration to fluids and more particularly, liquids. The fabric 70 is intended to be used in applications where fluids are splashed or sprayed onto the material and the material provides resistance to the direct pass through of a fluid. This fabric can be utilized in the medical field, hazardous waste field or other areas where people are interested in being protected from spilled or sprayed fluids.

FIG. 14 shows a protective gown 89 and FIG. 15 shows a protective facemask 91 that can be made using the layered fabric material 70. For the protective gown 89, the second layer of non-woven material 87 may be deleted if the gown is to be worn over clothes so that the inner surface of the gown does not contact the skin of the wearer. For both the protective gown 89 and the facemask 91, fluids that are spilled or sprayed will contact the outer layer 73 of the fabric. The fluid will pass through to the non-woven material 75 which provides resistance to fluid penetration. The fluid will then contact the thermoplastic film 79 having the angled capillaries 83. When the fluid engages the thermoplastic film 79, there is no direct path through the film and the velocity of the fluid is significantly reduced. The structure of the layered fabric 70 is intended to prevent direct passage of fluids and provides a much higher level of protection than the breathable materials that are currently available.

FIG. 16 shows the use of the thermoplastic film of the present invention in an absorbent pad or drape 88. In the structure, the film 79 is positioned on a layer of absorbent material 93. The film 79 is disposed so that the capillaries 83 that are formed by the perforations 81 are in contact with the absorbent material 93. With the structure the capillaries 83 act to wick fluid that is on the surface 85 of the thermoplastic film 79 to the absorbent material 93. The angle for the capillaries 83 prevent a direct line of sight along a line that is perpendicular to the surface of the film into the absorbent material 83 so that fluids that are contained in the absorbent material 83 are not easily visible when looking at the surface 85 of the film 79.

FIG. 17 shows another embodiment of a pad or drape 90 that can be made utilizing the film of the present invention. The film 79 is positioned with the surface 85 in contact with a layer of absorbent material 93. The film 79 is positioned so that the capillaries 83 formed by the perforations 81 extent in a direction away from the absorbent material 93. With the capillaries 83 extending away from the absorbent material 93, there is more resistance to strike through for a liquid that is under pressure, such as a sprayed or spilled liquid.

FIG. 18 shows the use of the thermoplastic film 79 as a landscape fabric 94. In this application, the film is positioned with the capillaries 83 extending towards the ground 95 upon which the film is to be positioned. The perforations 81 and the capillaries 83 allow moisture, such as rain, to pass through the film to the ground 95. However, the angled capillaries 83 effectively eliminate or minimize the amount of light that can pass through the film 79. This prevents weed growth and other undesirable growth in areas where the film is positioned. However, since rain can pass through the film, there is no difficulty with disposing of or pooling of rain water. In applications where additional strength is required, a non-woven material 97 can be laminated to the surface 85 of the film 79 to provide additional strength. It should also be understood that the non-woven material 97 can also be laminated to the opposite side of the film 79 to provide additional strength to the landscape fabric 94.

Figure 19:
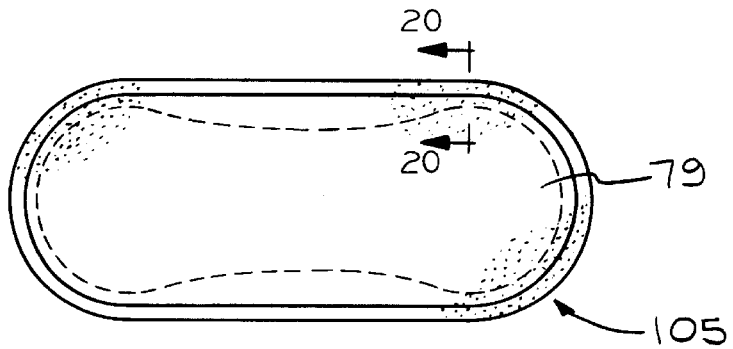
FIG. 19 shows a catamenial pad construction using the film of the present invention.
Figure 20:
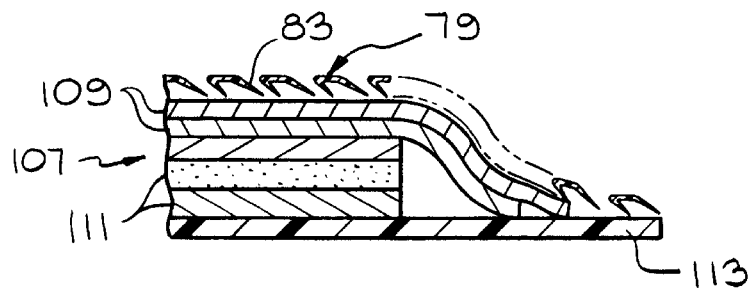
FIG. 20 is a cross-sectional view taken along line 20—20 in FIG. 19.

FIGS. 19 and 20 show a catamenial or feminine hygiene pad that can be constructed using the film of the present invention. The pad 105 has a layer of perforated thermoplastic film 79 that is positioned over an absorbent core 107. The film 79 is positioned so that the ends of the capillaries 83 that extend from film are in contact with the absorbent core 107. The absorbent core can include one or more layers of a non-woven material 109 and a highly absorbent wadding or gel material 111. A non-pervious thermoplastic film 113 is positioned on the side of the absorbent core 107 that is opposite to the film 79.

Figure 21:
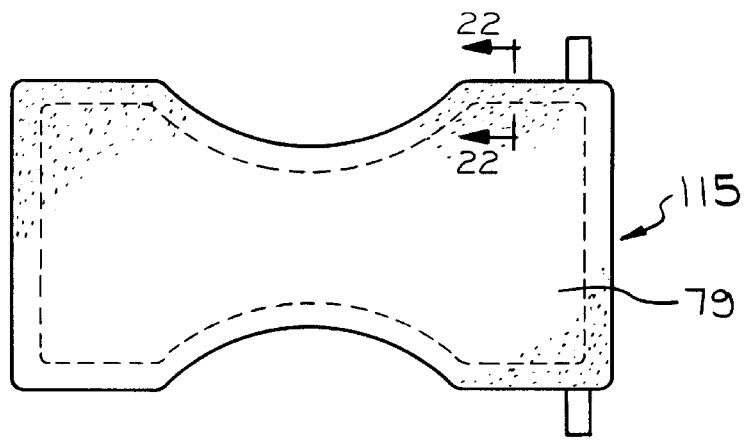
FIG. 21 shows a diaper construction using the film of the present invention.
Figure 22:
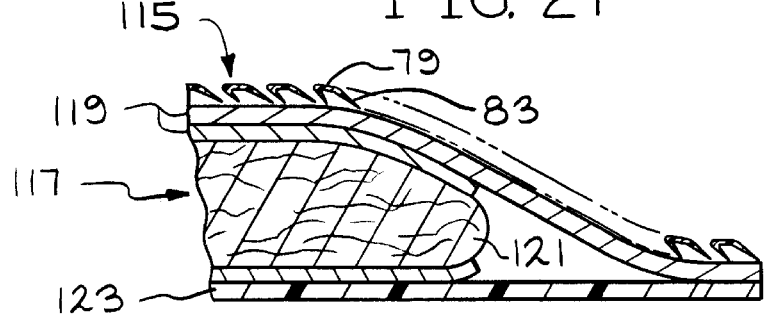
FIG. 22 is a cross-sectional view taken along line 21—21 in FIG. 21.

FIGS. 21 and 22 show a diaper product 115 that can be constructed using the film of the present invention. The diaper 115 has a layer of perforated thermoplastic film 79 that is positioned over an absorbent core 117. The film 79 is positioned so that the ends of the capillaries 83 that extend from the film are in contact with the absorbent core 117. The absorbent core can include one or more layers of a non-woven material 119 and a highly absorbent wadding or gel material 121. A non-pervious thermoplastic film 123 is positioned on the side of the absorbent core 117 that is opposite to the film 79.

It should be noted that the film layer 79 shown in FIGS. 19–22 will provide masking for fluid that is retained in the absorbent core material as previously discussed.

It should be understood that a film similar to the films shown in FIGS. 7, 8 and 9 can also be used as the film 79 in the applications shown in FIGS. 16–22.

The above description of the invention is given for the sake of explanation and various modifications and substitutions, other than those cited, can be made without departing from the scope of the following claims.

I claim:

1. A thermoplastic film comprising:

a first surface;

a second surface that is spaced apart from said first surface; and a plurality of perforations extending through said film, each perforation forming a capillary defined by a sidewall that is substantially cylindrical in shape and that extends from said second surface, said capillaries being disposed at an angle from about 5° to about 60° with respect to a plane that is perpendicular to said first surface, said angled capillaries preventing a direct line of sight through said capillary when viewed along the plane.

2. The film of claim 1, wherein said capillaries have an end that is spaced apart from said first surface of said film a distance from about 0.005 to about 0.050 of an inch.

3. The film of claim 1, wherein said perforations define a first opening in said first surface and said capillary terminates in a second opening that is spaced apart from said first surface, each of said first and second openings being substantially circular and each of said first and second openings having a center point.

4. The film of claim 3, wherein said center point of said first opening is displaced from said center point of said second opening.

5. The film 4, of claim wherein said center point of said second opening is displaced from said center point of said first opening a distance from about 5% to about 200% of a diameter of said first opening.

6. The film of claim 4, wherein said center point of said second opening is displaced from said center point of said first opening a distance from about 75% to about 125% of a diameter of said first opening.

7. The film of claim 1, wherein said thermoplastic film is a polyolefin film.

8. A thermoplastic film comprising:

a first surface;

a second surface that is spaced apart from said first surface; and a plurality of perforations extending through said film, each perforation forming a capillary defined by a sidewall that extends from said second surface and converges as said capillaries extend from said film, said capillaries being disposed at an angle from about 5° to about 60° with respect to a plane that is perpendicular to said first surface, said angled capillaries preventing a direct line of sight through said capillary when viewed along the plane.

9. The film of claim 8, wherein said sidewall of said capillaries converges in one direction.

10. A thermoplastic film comprising:

a first surface;

a second surface that is spaced apart from said first surface; and a plurality of perforations extending through said film, each perforation forming a capillary that extends from said second surface, each of said capillaries having a first portion that extends from said first surface at an angle (A) from abut 5° to about 60° with respect to a plane that is disposed perpendicular to said first surface and a second portion of said capillary that is disposed at an angle from about 5° to about 60° with respect to said plane, said second portion being positioned in the opposite direction to said first portion and preventing a direct line of sight through said perforations when viewed along the plane.

11. The film of claim 10, wherein said capillary defines a first opening in said first surface and terminates in a second opening that is spaced apart from said first surface of said film.

12. A thermoplastic film comprising:

a first surface;

a second surface that is spaced apart from said first surface; and a plurality of capillaries extending through said film, each capillary being defined by a sidewall that is substantially cylindrical in shape, said capillaries being disposed at an angle from about 5° to about 60° with respect to a plane that is perpendicular to said first surface, said angled capillaries preventing a direct line of sight through the capillaries when viewed along the plane.

\* \* \* \* \*